(12) United States Patent
Pham et al.

(10) Patent No.: US 9,418,203 B2
(45) Date of Patent: Aug. 16, 2016

(54) SYSTEMS AND METHODS FOR GENOMIC VARIANT ANNOTATION

(71) Applicant: Cypher Genomics, La Jolla, CA (US)

(72) Inventors: Phillip Pham, San Diego, CA (US); Salil Deshpande, San Diego, CA (US)

(73) Assignee: Cypher Genomics, Inc., La Jolla, CA (US)

( * ) Notice: Subject to any disclaimer, the term of this patent is extended or adjusted under 35 U.S.C. 154(b) by 219 days.

(21) Appl. No.: 13/841,575

(22) Filed: Mar. 15, 2013

(65) Prior Publication Data

US 2014/0280327 A1    Sep. 18, 2014

(51) Int. Cl.
*G06F 19/22* (2011.01)
*G06F 19/18* (2011.01)
*G06F 19/28* (2011.01)
*G06F 19/26* (2011.01)

(52) U.S. Cl.
CPC ............ *G06F 19/18* (2013.01); *G06F 19/28* (2013.01); *G06F 19/26* (2013.01)

(58) Field of Classification Search
CPC .......... G06F 19/18; G06F 19/28; G06F 19/26
See application file for complete search history.

(56) References Cited

U.S. PATENT DOCUMENTS

| | | | |
|---|---|---|---|
| 6,462,190 B1 | 10/2002 | Michikawa et al. | |
| 6,772,160 B2 | 8/2004 | Cho et al. | |
| 7,660,709 B2 | 2/2010 | Bugrim et al. | |
| 8,140,270 B2 | 3/2012 | Kingsmore et al. | |
| 8,392,353 B2 | 3/2013 | Cho et al. | |
| 8,417,459 B2 | 4/2013 | Reese et al. | |
| 8,489,334 B2 | 7/2013 | Chen et al. | |
| 2002/0160950 A1 | 10/2002 | Lal et al. | |
| 2003/0044864 A1 | 3/2003 | Short et al. | |
| 2003/0100995 A1 | 5/2003 | Loraine et al. | |
| 2003/0190649 A1 | 10/2003 | Aerts et al. | |
| 2004/0101876 A1 | 5/2004 | Mintz et al. | |
| 2004/0161779 A1 | 8/2004 | Gingeras et al. | |
| 2005/0032095 A1 | 2/2005 | Wigler et al. | |
| 2005/0214811 A1 | 9/2005 | Margulies et al. | |
| 2005/0281815 A1* | 12/2005 | Eshel ............... C07K 14/70578 424/144.1 |

(Continued)

FOREIGN PATENT DOCUMENTS

| | | |
|---|---|---|
| WO | WO 00/57309 A2 | 9/2000 |
| WO | WO 2005/071058 A2 | 8/2005 |

(Continued)

OTHER PUBLICATIONS

Ashley et al., Clinical evaluation incorporating a personal genome, Lancet (May 2010) 375(9725): 1525-1535. doi:10.1016/S0140-6736(10)60452-7.

(Continued)

*Primary Examiner* — Tarek Chbouki
(74) *Attorney, Agent, or Firm* — Knobbe, Martens, Olson & Bear, LLP

(57) ABSTRACT

A system for annotating genomic variant files includes an application server, an annotation database, a genomic database, and an annotation processing computer system. The genomic database may be graph-oriented. The annotation processing computer system processes can process variant files in batch modes and includes annotation modules designed to improve the speed of the annotation process. The batch modes may include batch transmission, and/or batch annotation.

20 Claims, 7 Drawing Sheets

(56) References Cited

U.S. PATENT DOCUMENTS

| | | |
|---|---|---|
| 2006/0142949 A1 | 6/2006 | Helt et al. |
| 2006/0195428 A1 | 8/2006 | Peckover et al. |
| 2007/0042380 A1 | 2/2007 | Bentwich et al. |
| 2007/0172853 A1* | 7/2007 | McCarroll ............ C12Q 1/6827 435/6.16 |
| 2008/0243551 A1 | 10/2008 | Subramaniam |
| 2009/0083268 A1 | 3/2009 | Coqueret et al. |
| 2009/0252046 A1 | 10/2009 | Canright et al. |
| 2009/0299640 A1* | 12/2009 | Ellis et al. ........................ 702/19 |
| 2009/0307181 A1 | 12/2009 | Colby et al. |
| 2010/0291681 A1 | 11/2010 | Khvorova et al. |
| 2010/0318528 A1* | 12/2010 | Kupershmidt et al. ....... 707/756 |
| 2011/0060532 A1 | 3/2011 | Gladding et al. |
| 2011/0098193 A1 | 4/2011 | Kingsmore et al. |
| 2011/0143344 A1* | 6/2011 | Goate .................... A61K 31/00 435/6.11 |
| 2011/0183924 A1 | 7/2011 | Mintz et al. |
| 2012/0077682 A1 | 3/2012 | Bowcock et al. |
| 2012/0078901 A1 | 3/2012 | Conde et al. |
| 2012/0102041 A1 | 4/2012 | Park et al. |
| 2012/0102054 A1 | 4/2012 | Popescu et al. |
| 2012/0191366 A1 | 7/2012 | Pearson et al. |
| 2012/0214159 A1 | 8/2012 | George et al. |
| 2012/0214163 A1 | 8/2012 | Sugarbaker et al. |
| 2012/0230326 A1* | 9/2012 | Ganeshalingam et al. ... 370/389 |
| 2013/0091126 A1* | 4/2013 | Krishnaswami et al. ..... 707/722 |
| 2013/0267425 A1* | 10/2013 | Liao ..................... C12Q 1/6883 506/2 |
| 2013/0311106 A1* | 11/2013 | White ..................... G06F 19/20 702/20 |
| 2013/0332081 A1* | 12/2013 | Reese ..................... G06F 19/18 702/19 |
| 2014/0121116 A1* | 5/2014 | Richards et al. .................. 506/2 |
| 2014/0121120 A1 | 5/2014 | Chen et al. |
| 2014/0310215 A1* | 10/2014 | Trakadis ......................... 706/13 |
| 2014/0359422 A1* | 12/2014 | Bassett et al. ................. 715/230 |

FOREIGN PATENT DOCUMENTS

| | | |
|---|---|---|
| WO | WO 2007/016668 A2 | 2/2007 |
| WO | WO 2009/058383 A2 | 5/2009 |
| WO | WO 2009/127693 A1 | 10/2009 |
| WO | WO 2012/029080 A1 | 3/2012 |
| WO | WO 2012/034030 A1 | 3/2012 |
| WO | WO 2012/098515 A1 | 7/2012 |
| WO | WO 2012/104764 A2 | 8/2012 |
| WO | WO 2013/009890 A2 | 1/2013 |
| WO | WO 2013/019987 A1 | 2/2013 |
| WO | WO 2013/049702 A2 | 4/2013 |
| WO | WO 2013/067001 A1 | 5/2013 |
| WO | WO 2013/070634 A1 | 5/2013 |
| WO | WO 2014/149972 A1 | 9/2014 |
| WO | WO 2014/151088 A2 | 9/2014 |

OTHER PUBLICATIONS

Bansal et al., Statistical analysis strategies for association studies involving rare variants, Nat Rev Genet. (Nov. 2010) 11: 773-785.

ClinVar Overview, National Society of Genetic Counselors, www.ncbi.nim.nih.gov/clinvar/—(Downloaded Jul. 2014).

Dering et al., Statistical analysis of rare sequence variants: an overview of collapsing methods, Genet Epidemiol. (2011) 35(suppl 1): S12-S17.

Emily et al., Using biological networks to search for interacting loci in genome-wide association studies, Eur J Hum Genet (2009) 17(10): 1231-40, supplemental data.

Haggerty et al., A strategy for identifying transcription factor binding sites reveals two classes of genomic c-Myc target sites, Proc Acad Sci USA (2003) 100(9): 5313-5318.

Kim et al., CNVRuler: A copy number variation-based case-control association analysis tool, Bioinformatics (2012) 28(13).

Kircher et al., A general framework for estimating the relative pathogenicity of human genetic variants, Nat Genet. (2004) 46(3): 310-315.

Korodi et al., A universal algorithm for random-access compression and applications for annotated DNA sequences, Conference: Genomic Signal Processing and Statistics, 2007. GENSIPS 2007.

Li et al., Methods for detecting associations with rare variants for common diseases: application to analysis of sequence data, Am. J. Human Genetics (2008) 83: 311-321, supplemental data.

Mooney, Bioinformatics approaches and resources for single nucleotide polymorphism functional analysis, Brief Bioinform (2005) 6(1): 44-56.

Mossé et al., Identification of ALK as the major familial neuroblastoma predisposition gene, Nature (2008) 455(7215): 930-935. doi: 10.1038/nature07261.

O'Connor et al., SeqWare Query Engine: storing and searching sequence data in the cloud, BMC Bioinformatics (2010) 11(Suppl 12):S2.

Shetty et al., SeqAnt: A web service to rapidly identify and annotate DNA sequence variations, BMC Bioinformatics (2010) 11:471.

Torkamani et al., Accurate prediction of deleterious protein kinase polymorphisms, Bioinformatics (2007) 23(21): 2918-2925.

Torkamani et al., Clinical implications of human population differences in genome-wide rates of functional genotypes, Front Genet. (2012) 3(211): 1-19.

Torkamani et al., Identification of rare cancer driver mutations by network reconstruction, Genome Res. (2009) 19: 1570-1578.

Torkamani et al., Predicting functional regulatory polymorphisms, Bioinformatics (2008) 24(16): 178701792.

Torkamani et al., Prediction of Cancer Driver Mutations in Protein Kinases, Cancer Res (2008) 68(6): 1675-1682.

Torkamani et al., Prestige centrality-based functional outlier detection in gene expression analysis, Bioinformatics (2009) 25(17): 2222-2228.

Tute Genomics—Product Homepage, www.tutegenomics.com/product (Downloaded Jul. 2014).

Tute Genomics—Annotations included in the Tute Genomics Web Platform www.tutegenomics.com (Downloaded Jul. 2014).

Van Zeeland et al., Evidence for the role of EPHX2 gene variants in anorexia nervosa, Mol Psychiatry (2014) 19: 724-732.

Wang et al., Annovar: functional annotation of genetic variants from high-throughput sequencing data, Nucl Acids Res. (2010) 38(16): e164. doi: 10.1093/nar/gkq603.

Yandell et al., A probabilistic disease-gene finder for personal genomes, Genome Res. (2011) 21(9): 1529-1542.

Zeller et al., An integrated database of genes responsive to the Myc oncogenic transcription factor: identification of direct genomic targets, Genome Biology (2003) 4:R69.

Zhang et al., A general framework for weighted gene co-expression network analysis, Stat Appl Genet Mol Biol. (2005) 4:Article 17. Epub Aug. 12, 2005.

Zhao et al., CNVannotator: A comprehensive annotation server for copy number variation in the human genome, PLoS One (2013). doi: 10.1371/journal.pone.0080170.

Boeckmann et al., The SWISS-PROT protein knowledgebase and its supplement TrEMBL in 2003, Nucl. Acids Res. (2003) 31 (1):365-370.

Karchin et al., LS-SNP: large-scale annotation of coding non-synonymous SNPs based on multiple information sources, 21(12): 2814-2820 (2005) doi: 10.1093/bioinformatics/bti442.

Karchin, Next generation tools for the annotation of human SNPs, Brief Bioinform (2009) 10 (1): 35-52.

Lee et al., F-SNP: computationally predicted functional SNPs for disease association studies, Nucl. Acids Res. (2007) 36 (suppl 1): D820-D824.

Yuan et al., FASTSNP: an always up-to-date and extendable service for SNP function analysis and prioritization, Nucl. Acids Res. (2006) 34 (suppl 2): W635-W641.

Specification, Claims, Abstract and Figures from U.S. Appl. No. 61/545,895, filed Oct. 11, 2011 (Priority application of U.S. Appl. No. 13/648,999, Krishnaswami et al.).

Specification, Claims, Abstract and Figures from U.S. Appl. No. 61/545,922, filed Oct. 11, 2011 (Priority application of U.S. Appl. No. 13/648,999, Krishnaswami et al.).

(56) References Cited

OTHER PUBLICATIONS

Specification, Claims, Abstract and Figures from U.S. Appl. No. 61/598,499, filed Feb. 14, 2012 (Priority application of U.S. Appl. No. 13/648,999, Krishnaswami et al.).
Specification, Claims, Abstract and Figures from U.S. Appl. No. 61/5640,389, filed Apr. 30, 2012 (Priority application of U.S. Appl. No. 13/648,999, Krishnaswami et al.).
Iordanov, Borislav, HyperGraphDB: A Generalized Graph Database, Web-Age Information Management: WAIM 2010 International Workshops, LNCS 6185 (2010) 25-36.
Communication Relating to the Results of the Partial International Search Report for Application No. PCT/US2014/024957, mailed Nov. 13, 2014.
International Search Report and Written Opinion for Application No. PCT/US2014/024957, mailed Jan. 23, 2015.
ACMG, Standards and Guidelines for Clinical Genetics Laboratories; 2006 edition; pp. 1-23.
Richards et al., ACMG recommendations for standards for interpretation and reporting of sequence variations, 2007, Molecular Working Group of the ACMG Quality Committee, pp. 1-7.

* cited by examiner

Analysis Results

CLINFILTER - IDIOPATHIC IBC_01

RANK DATA ← BACK TO GENOME VARIANT VIEWER ← BACK TO VIEW ANALYSIS

| RANK | CHR | BEGIN | END | VAR TYPE | REFERENCE | ALLELE | GENE | CODING IMPACT | ORIGINAL AA | ALLELE AA | DBSNP ID |
|---|---|---|---|---|---|---|---|---|---|---|---|
| 1 | chrX | 123020119 | 123020120 | snp | G | A | XIAP(uc010nqu.2)<br>XIAP(uc004eix.2)<br>XIAP(uc010nqv.2) | Nonsynonymous<br>Nonsynonymous | C<br>C | Y<br>Y | |
| 2 | chr21 | 45709655 | 45709656 | snp | C | T | AIRE(uc002zei.2) | Nonsense | R | | |
| | | | | | | | IGF1R(uc010urq.1) | Nonsynonymous | R | H | rs121434254 |

SHOW SUMMARY    EXPORT

FIG. 7

SYSTEMS AND METHODS FOR GENOMIC VARIANT ANNOTATION

BACKGROUND OF THE DISCLOSURE

Description of the Related Art

The availability of high-throughput DNA sequencing technologies has enabled nearly comprehensive investigations into the number and types of sequence variants possessed by individuals in different populations and with different diseases. For example, not only is it now possible to sequence a large number of genes in hundreds if not thousands of people, but it is also possible to sequence entire individual human genomes in the pursuit of inherited disease-causing variants or somatic cancer-causing variants. Whole genome sequencing as a relatively routine procedure may lie in the near future as high-throughput sequencing costs and efficiency continue to improve. In fact, as costs continue to decline, high-throughput sequencing is expected to become a commonly used tool, not only in human phenotype based sequencing projects, but also as an effective tool in forward genetics applications in model organisms, and for the diagnosis of diseases previously considered to be idiopathic, for which there are already some striking examples.

Once a sequence is obtained, an effort is made to identify the location and character of those portions of a sequence that differ from one or more "standard" reference sequences, with each difference commonly referred to as a variant. This can help identify those portions of an individual's genome that could potentially contribute to a clinical condition or other trait of the individual. For example, it is common to compare the sequence of a particular individual with reference human genome sequences maintained by the University of California, Santa Cruz, and create a list of the variants that exist between an individual's sequence and a reference sequence.

This variant list may include millions of variants, but provides little if any information on the impact any particular variant may have on gene function. Research programs around the world are continually gathering information relating particular variants to gene function, disease states, and the like. Furthermore, a variety of computational methods have been developed to deduce possible physiological effects of some types of variants based on their location on the genome and the nature of the variant, even if no laboratory biochemical or clinical studies have been undertaken on that particular variant.

Collecting and/or producing such information about the variants in a given individual's genome is a large task, and computer implemented methods of "annotating" variants by accessing and searching publicly available databases and computing predicted variant-function relationships in an automated manner have been developed. However, given the large number of variants present in a typical genome, the process is still time consuming, and limits the use of genome sequence information in clinical and research applications even though the potential benefits of prompt, inexpensive access to this information are widely appreciated.

SUMMARY

In one embodiment, an electronic computer system for the automated annotation of genomic variants comprises an application server computer system configured to receive one or more variant files from a client computer system different from the application server computer system, an annotation processing computer system different from the application server computer system and the client computer system and configured to receive one or more variant files from the application server computer system, an annotation database accessible by both the application server computer system and the annotation processing computer system. The annotation processing computer system is configured to annotate variants in the variant files received from the application server computer system and store variant annotation results in the annotation database, and the application server computer system is configured to retrieve variant annotation results from the annotation database and deliver retrieved variant annotation results to the client computer system.

In another embodiment, a computer implemented method of transferring variant files containing information defining genomic variants derived from genome sequence data from a first computer system to a second computer system. The method comprises with a computer processor, identifying a plurality of separate variant files present on the first computer system, with a computer processor, combining at least some data in the separate variant files into a single variant file, and with a computer processor, transferring the single variant file to the second computer system.

In another embodiment, a non-transient computer readable memory storing a database of genomic information, wherein the genomic information comprises a plurality of different variants found in whole or partial genomic sequences of a plurality of different subjects. Data identifying each of the plurality of different variants are stored as a first plurality of nodes of a graph oriented database scheme, data identifying each of the plurality of different subjects are stored as nodes of the graph oriented database scheme, and the presence of a variant in a subject is stored as an edge connecting the variant and the subject in the graph oriented database scheme.

In another embodiment, a computer implemented method of annotating a plurality of genomic sequence variants comprises with a computer processor, identifying the chromosome on which each variant is located, and with a computer processor, generating annotations for a first set of annotation types for each of the variants in a plurality of parallel processes, the plurality of parallel processes corresponding to the different chromosomes on which the variants are located.

In another embodiment, a computer implemented method of annotating a plurality of genomic sequence variants comprises defining a plurality of groups of annotation types, the groups comprising different annotation types from each other, and with a computer processor, generating annotations for each of the variants in a plurality of parallel processes, the plurality of parallel processes corresponding to the plurality of groups.

In another embodiment, a computer implemented method of annotating a set of variants found in a plurality of whole or partial genome sequences of a corresponding plurality of subjects comprises with a computer processor, identifying multiple instances of at least one variant present in the set of variants, with a computer processor, producing a second set of variants having only one instance of the identified at least one variant, and with a computer processor; generating annotations for the second set of variants.

In another embodiment, an electronic computer system for generating annotations of a plurality of different types for genomic variants found in the whole genome sequences of a plurality of subjects, each subject having at least one million variants to be annotated. The system comprises a computer system configured to receive the genomic variants, separate the genomic variants into variant groups, separate the annotations into annotation groups, and perform parallel processing based at least in part on one or both of the variant groups or annotation groups. In some embodiments, the computer system generates at least 80 annotations for each variant at a rate of one hour per whole genome or faster.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein:

FIG. 7 is an example user interface that may be generated and presented to a user to customize and view genomic variant analysis and annotation results in a table format.

DETAILED DESCRIPTION

Various embodiments of systems, methods, processes, and data structures will now be described with reference to the drawings. Variations to the systems, methods, processes, and data structures which represent other embodiments will also be described. Certain aspects, advantages, and novel features of the systems, methods, processes, and data structures are described herein. It is to be understood that not necessarily all such advantages may be achieved in accordance with any particular embodiment. Accordingly, the systems, methods, processes, and/or data structures may be embodied or carried out in a manner that achieves one advantage or group of advantages as taught herein without necessarily achieving other advantages as may be taught or suggested herein.

Figure 1:
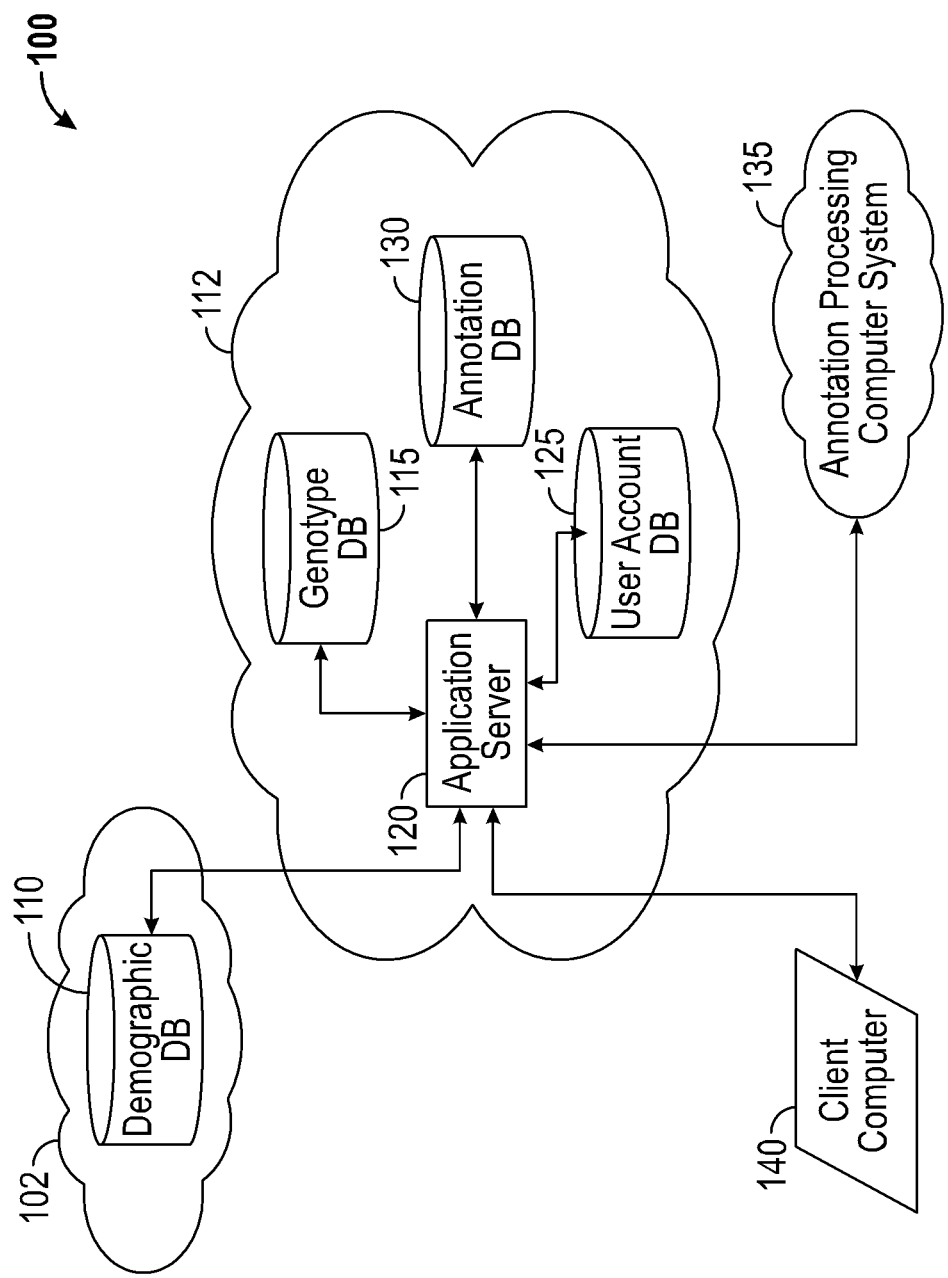
FIG. 1 is a block diagram illustrating one embodiment of a computer system architecture for genomic variant analysis.

FIG. 1 is a block diagram illustrating one embodiment of a computer implemented system 100 for genomic variant annotation. The system 100 illustrated in FIG. 1 is implemented as a Software as a Service (SAS) type system. It will be appreciated, however, that instead of being connected through a wide area network (WAN) such as the Internet, the components illustrated in FIG. 1 can be located together. When located together, some or all of the different computing systems illustrated in FIG. 1 may be combined such that the functions described below are performed on a single computer system. Some or all of the system components illustrated in FIG. 1 can also be incorporated into other systems, such as sequencing machines, and/or Laboratory Information Management Systems (LIMS) and/or Electronic Medical Record (EMR) systems.

In the SAS environment illustrated in FIG. 1, a client computer 140 may receive a client software package from the application server 120. This client software package may be used by the client computer 140 to upload one or more variant files and/or variant file lists to the application server 120. As will be described in further detail below, the system 100 takes the uploaded variant information and processes the variant information to produce annotation data for at least some, but usually all of the variants in each uploaded variant file. Specific types of annotation data that may be generated by the system 100 are described further below. Generated annotation data is stored within the system 100 and some or all of the annotation data may be returned to the client computer 140 in various ways and forms. The systems and methods described herein are especially applicable to variant files derived from any organism sequence or partial sequence, but are especially useful when the variant files are derived from whole genome sequences, which for the human genome is about 3 billion base pairs (and which may or may not include a mitochondrial DNA sequence), and which will result in a variant file with usually at least hundreds of thousands, and more likely millions of variants.

The variant list uploaded by the client computer may be in the format of any currently known sequence variant file format such as the Variant Call Format ("VCF"), Complete Genomics, Inc. ("CGI") variant file format, or any other file format. Although the system shown in FIG. 1 has a variant file being transferred from the client computer 140 to the application server 120, in other embodiments, the client computer may upload sequence data itself such as in a BAM and/or SAM format, and the application server 120 or another computer system can perform a conventional process of variant extraction to produce a variant file for annotation. Such genomic sequence data in a BAM and/or SAM format may need to be aligned before being processed to extract variant information.

The annotation data returned to the client computer can include all the annotation data generated by system 100 or portions of the annotation data generated by system 100. The annotation data delivered to the client computer 140 may be simply one or more flat files with populated pre-defined annotation fields associated with all or a portion of the variants in the variant file uploaded to the application server 120. The client computer may request particular portions of the annotation data generated by system 100 for the variants. In some implementations, the software package received from the application server 120 includes a genome browser program with a Graphical User Interface GUI allowing a user of the client computer to produce various visualizations of the variant data of a selected genome, run queries on the generated annotation data, filter genome variants through various filters for focusing on variants with particular characteristics as defined by their associated annotations, and otherwise navigate through the variants and annotation data generated by the system 100 in a user friendly way. One embodiment of such an annotation data user interface is described in further detail below.

In some embodiments, a user account database 125 may store information related to users who are authorized to access the system or view analysis results. The information stored in the user account database 125 may include login information such as user account and password, a period of subscription, and/or address, payment, and other related information.

Variant files typically (though not necessarily) each contain a list of variants found during the sequencing of one individual. As noted above, systems described herein are especially applicable to variant files containing variants for a whole genome sequence of an individual, and may contain millions of identified variants. Additional details of advantageous upload processes, including variant file conversion and/or compression, are explained further below.

To initiate the annotation process, an interface on the client computer 140 may be presented to a user to identify variant files stored on the client computer 140 to be uploaded to the application server 120. This information is sent to the application server 120, which generates a unique file ID for each variant file to be uploaded that is returned to the client computer 140 upon successful upload, and which the user can use to obtain annotation status information and to access the annotation data generated from the file after the annotation process is complete. In the system 100, the uploading process of the variant files can be optimized in a variety of ways. Variant files such as VCF files are generally simple text files in a tab or comma separated value format. VCF files can include a wide variety of columns, not all of which are necessary for the annotation process performed by the system 100.

To reduce the amount of data to be transferred, the software package on the client computer 140 can extract information from only the relevant columns of the VCF or other variant file format for transmission to the application server 120. For example, extracted variant data for downstream analysis may include: haplotype information, the chromosome where a variant is located; the start position of a variant; the end position of a variant; variant type (such as Single Nucleotide Polymorphism (SNP), Deletion, Insertion, a Block Substitution, and so forth); reference sequence; allele sequence; genotype information (may use "N" for bases not called; "0/1" for heterozygous variant; "1/1" for homozygous variant); genotype quality score; variant quality score; and read depth. This data can be reformatted into a new tab separated value text file with only these columns, and this text file is compressed, encrypted, and uploaded to the application server 120 from the client computer 140.

The software package on the client computer 140 can also include the ability to upload phenotype information from the individual associated with a given uploaded variant file. Such information may include gender, race, personal identification information, medical history, current diagnosis and so forth. Because this information can be confidential, and in order to comply with federal and state law requirements for healthcare related information, such as HIPPA (Health Insurance Portability and Accountability Act of 1996), a separate demographic database 110 may be implemented in a computer system that is separated from the other databases of the system. For example, in some cases, the demographic database may be separately implemented in a "private cloud" computer environment, whereas the remainder of the system 100 is implemented in a "public cloud" computer environment. Access to the demographic database 110 is controlled by the application server 120, which may utilize a non-public IP address that is the only means for accessing the data on the demographic database. The physical computer(s) on which demographic data resides may also be located in a physically secure area with access limited to authorized personnel at the datacenter at which it is located. The application server 120 may authenticate access requests, query requests, and/or other requests regarding the demographic database 110 to ensure the security of this data. The demographic data may be stored in association with the file ID assigned by the application server 120 to the associated variant file. In some cases, demographic information may be determined during the process of genomic variant analysis and stored in a demographic database 110. For example, information regarding a person's ethnicity may be determined based on variants in the person's genomic sequence data, and such information may also be stored in the demographic database 110.

Figure 2:
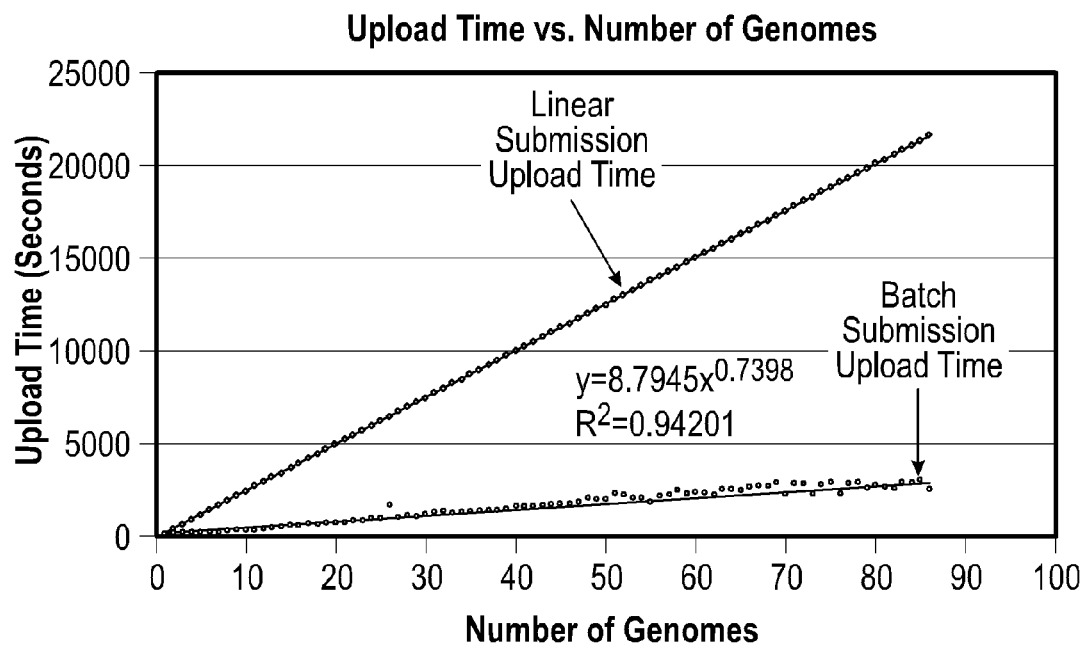
FIG. 2 is a diagram illustrating processing speed improvements of batch variant file uploading.

If the client computer indicates that multiple variant files are to be uploaded, the software on the client computer can combine these separate variant files into a temporary single variant file, with the variant files within the larger temporary file delimited by an additional header row or other method. This larger file may then be compressed, encrypted, and uploaded to the application server 120. Because encryption algorithms can run much faster for the same amount of data if the data is in one large file rather than multiple small files, this greatly reduces the time required to transfer the variant files to the application server 120, as illustrated in FIG. 2. After transmission, the temporary file may be deleted. This process may be transparent to the user of the client computer system 140.

After the application server receives the variant file from the client computer, it may in turn upload the variant file and the file ID to the annotation processing computer system 135. In some embodiments, the annotation computer processing system 135, under the control of the application server 120, may use multi-server, multi-threading, and parallel computing technologies to thoroughly annotate large numbers of whole-genome variant files in a short amount of time. In some embodiments, the annotation pipeline 135 is implemented in a High-Performance Computing (HPC) environment that may have dedicated computing nodes and/or computing nodes assigned by an automatic load balancer under the control of the application server 120.

Figure 3A:
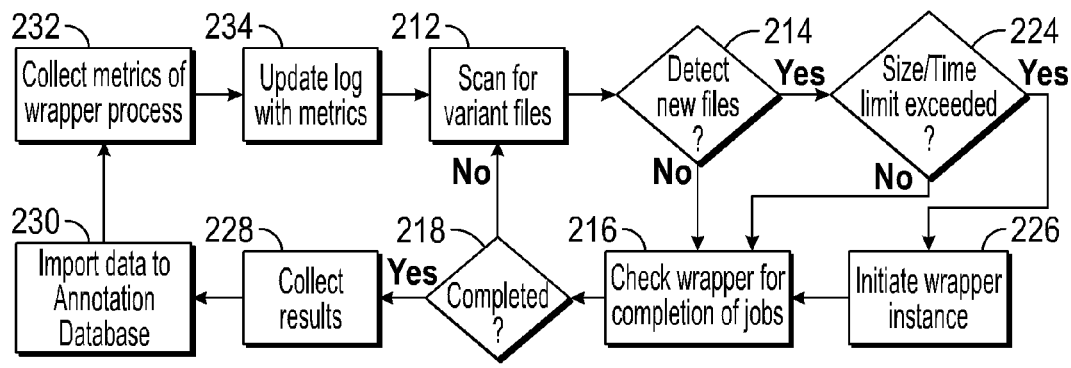
FIGS. 3A and 3B are flowcharts that illustrate one embodiment of a process of annotating genomic variant data in a workflow optimized for processing speed and annotation coverage.

Annotation processing computer system 135 runs an annotation controller routine 208 (FIG. 3A), which may operate as described with reference to FIG. 3B. At block 212 the annotation controller routine checks a file system folder or other storage location where the application server 120 pushes variant files for annotation by computer system 135 that have been received from client computer 140. If no new files are detected at decision block 214, the annotation controller routine checks for completed annotation projects at block 216. If there are none, the routine loops back to search again for uploaded variant files from application server 120.

When an uploaded variant file or files are found at decision block 214, the annotation controller routine checks the total size of variant files currently in the queue for processing, and also checks the total time the oldest variant file has been waiting to be processed at decision block 224. If either the total file size is greater than a threshold, or the oldest variant file wait time is greater than a threshold, then the annotation controller initiates an annotation wrapper instance at block 226 and issues it to the computer system that generates the annotations. The size threshold may, for example, be set at 6 million variants total for all files in the queue, and the time threshold may be 10 minutes. When the stored queue of variant files is cleared and being processed, the annotation controller routine again checks for completion of any previously issued wrapper instances at block 216. If this time one or more are found, the results of the previous instance are collected at block 228, and the results are uploaded to the annotation database 230. Furthermore, processing metrics for the completed instance are collected at block 232, and a log of these metrics is updated with the value of the new metrics at block 234. In some embodiments, the collected metrics may include the number of variants annotated in the completed instance, the individual Central Processing Unit (CPU) time for each processing module (the processing modules are described further below), total CPU time to generate the annotations, and total linear time to produce the annotations. The annotation processing computer system may also send a message to the application processor that an annotation wrapper has been completed, and the annotation database 130 has been updated with annotation information for one or more variant files.

This process flow and task allocation is advantageous because the process of variant annotation is dedicated to the annotation processing computer system 135, which is preferably an especially high throughput, high performance system, whereas other processes such as uploading variant files, delivering results to the client computer 140, building the genotype database 115 (described further below), and the like can be handled independently by the application server 120. This allows the annotation processing to be completed in parallel with these other processes, and allows different computer system types from different vendors to be used for the specific tasks they are designed for, increasing the speed of the system 100 and reducing the cost of operating the system 100.

Figure 3B:
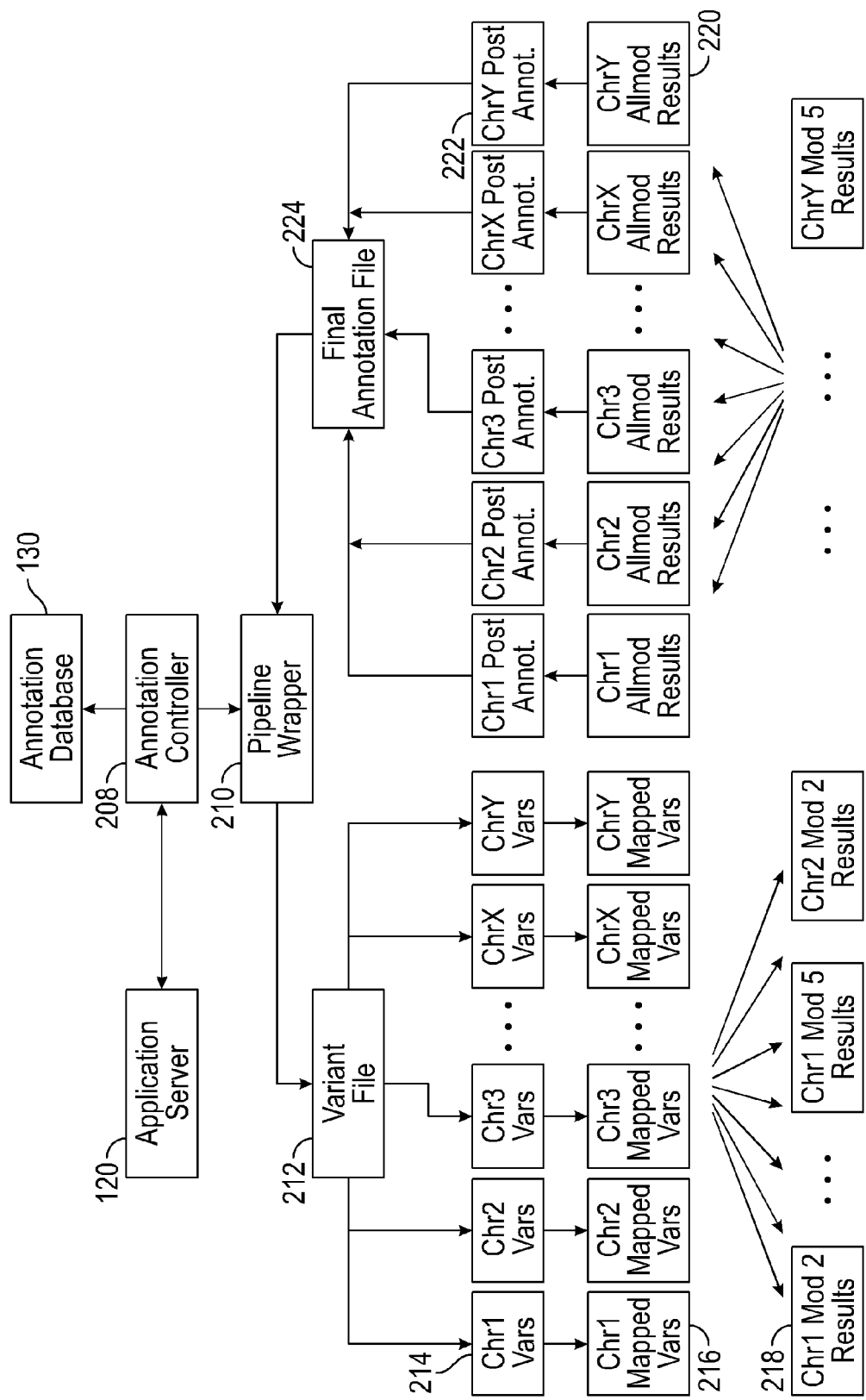

Turning now to the actual process of creating the annotations, FIG. 3B is a block diagram of one example process that has been found to perform a large number of annotations in a very short amount of time. The annotations that are produced in one implementation of the system of FIG. 1 and an example syntax for the fields are set forth below. The below syntax, delimiter definitions, are specific examples only, and may be defined in a variety of alternative ways.

Eleven of the annotations can generally be obtained directly from the original variant file:

1. Haplotype: Haplotype information, if available
   If no information is available, any generic symbol such as '-' or '.'
2. Chromosome: Chromosome containing the variant
   syntax: 'chr1', 'chr22', 'chrX', 'chr1_gl000191_random', etc
3. Begin: Start position of the variant
   0-based, NCBI37/hg19 coordinates
4. End: End position of the variant
   0-based, NCBI37/hg19 coordinates
5. VarType: Variant type
   'snp'—single nucleotide polymorphisms
   'del'—deletion
   'ins'—insertion
   'delins'—substitution
6. Reference: Reference nucleotide sequence
   'A', 'C', 'G', 'T' nucleotides only
7. Allele: Variant nucleotide sequence
   'A', 'C', 'G', 'T' nucleotides only
8. Genotype: Genotype information
   '0/1'—heterozygous variant
   '1/1'—homozygous variant
   For unknown haplotype call, replace with 'N' (i.e. '1/N', etc.)
   If no information is available, any generic symbol such as '-' or '.'
9. GenotypeQual: Genotype quality score, if available
   If no information is available, any generic symbol such as '-' or '.'
10. VariantQual: Variant quality score, if available
    If no information is available, any generic symbol such as '-' or '.'
11. ReadDepth: Read Depth, if available
    If no information is available, any generic symbol such as '-' or '.'

The remaining generated annotations are computed from information in the variant file and information retrieved from reference human genome builds and databases of genomic information, and are set forth below:

1a.) Gene: Nearest gene names with different transcripts or genes on opposite strands separated by '////'
   Note: Order of all annotation results correspond to order of transcripts separated by '////'
1b.) Gene_Type: Type of gene
   Values: 'Protein-Coding', 'Noncoding_RNA'
1c.) Location: Variant location in relation to gene (e.g. 'exon', 'intron', '3UTR', '5utr', 'upstream', 'downstream'.)
   Note: Deletion and block substitutions will display span of mutation (e.g. 'exon_6-intron_6')
1d.) Distance: Distance from nearest gene transcription start or stop site
   Note: Value is 0 if variant falls within a gene
1e.) Coding_Impact: Mutation effect in coding region. (Note: differentiated between transcripts by '////' as ordered in 1a from above)
   Synonymous: no amino acid change
   Nonsynonymous: amino acid change
   Nonsense: stop codon mutation
   In_Frame_Insertion: Insertion of one amino acid in protein sequence
   InterCodon_In_Frame_Insertion: mid-codon insertion of triplet sequence(s)
   In_Frame_Deletion: deletion of one amino acid in protein sequence
   In_Frame_Deletion_One_Altered_Codon: mid-codon deletion of triplet sequence(s)
   In_Frame_Rearrangement: block substitution of equal bases
   Frameshift: change in reading frame
   Complex: other block substitutions
1f.) Protein_Pos: Amino acid position in protein sequence
   Note: Deletions and block substitutions will display span of mutation (e.g. 'exon_6-intron_6')
1g.) Original_AA: Original amino acid
   Note: 'ins' mutations excluded
1h.) Alternate_AA: Mutant amino acid
   Note: 'ins' mutations excluded
1i.) Start~Stop_Dist: Distance of variant from start and stop codon of the transcript
   Note: separated by '~' and differentiated between transcripts by '////' as ordered in 1a from above
1j.) Prop_Cons_Affected_Upstream: Proportion of affected, conserved, coding sequence upstream of the mutation.
   Note: Differentiated between transcripts by '////' as ordered in 1a from above
1k.) Prop_Cons_Affected_Downstream: Proportion of affected, conserved, coding sequence downstream of the mutation
   Note: Differentiated between transcripts by '////' as ordered in 1a from above
1l.) Trunc_Prediction: Damaging truncation prediction for frameshift/nonsense variants
   Note: Differentiated between transcripts by '////' as ordered in 1a from above 2.) Conserved**: Conservation scores from various sources
  Format: PhastCons conserved element log-odds score ~ PhyloP position specific log p-
    value of conservation (e.g. 'lod=59~0.691')
  Note: ** indicates level of conservation considered, e.g. Primates, Mammals etc.
3a.) ***_minallele: Frequency of alternate allele at variant position, if known, in the HapMap dataset
  Note: *** indicates population (e.g. CEU, YRI, etc.)
  Format: 400 = 40% allele frequency
3b.) 1000GENOMES_AF: Frequency of alternate allele at variant position, if known, in the 1000 genomes dataset
3c.) CG_69_AF: Frequency of alternate allele at variant position, if known, in the Complete Genomics 69 genomes diversity panel
3c.) CG_WELLDERLY_AF: Frequency of alternate allele at variant position, if known, in the Wellderly dataset
4a.) eQTL_genes: Genes with affected expression levels (variant-specific)
5a.) miRNA_BS_influenced: Name of microRNA with an affected binding site (TargetScan) (direct/indirect impact)
  Note: separated by '~' and differentiated between transcripts by '////' as ordered in 1a
    from above
5b.) miRNA_BS_impact: miRNA binding site deletion/creation effect
  Note: separated by '~' as ordered in 5a and differentiated between transcripts by '////'
    as ordered in 1a from above
6a.) miRNA_BS_direct: Name of microRNA with an affected binding site (direct impact only)
  Note: Differentiated between transcripts by '////' as ordered in 1a from above
6b.) miRNA_BS_deltaG: Change in Gibbs Free Binding Energy between miRNA and 3'UTR binding site
  Note: separated by '////' as ordered in 6a
7a.) miRNA_genomic: Name of pre-microRNA sequence that is perturbed
7b.) miRNA_folding_deltaG: Change in minimum free energy of secondary structure of pre-microRNA
  Note: separated by '////' as ordered in 7a
7c.) miRNA_binding_deltaG: Average change in Gibbs Free Binding Energy of miRNA to predicted 3'utr binding sites
7d.) miRNA_top_targets_changed: Top 5 genes with largest change in Gibbs Free Binding Energy between microRNA sequence and 3'utr binding site
8a.) Splice_Site_Pred: Splice site acceptor/donor disruption
  Entries: Splice Site Acceptor Damaged, Splice Site Donor Damaged
8b.) Splicing_Prediction(MaxENT): Result of MaxENT splice site prediction
  Format: Splice site prediction~wild-type maximum entropy score&variant maximum
    entropy score (e.g. 'Splicing_Change~4.28&-16.13')
  Note: Differentiated between transcripts by '////' as ordered in 1a from above
9a.) ESE_sites: Number of exonic splicing enhancer motifs perturbed (e.g. '2 site(s) CREATED', '1 site(s) DELETED', etc.)
  Note: Differentiated between transcripts by '////' as ordered in 1a from above
9b.) ESS_sites: Number of exonic splicing silencer motifs perturbed (e.g. '1 site(s) CREATED', '2 site(s) DELETED')
  Note: Differentiated between transcripts by '////' as ordered in 1a from above
10a.) Protein_Impact_Prediction(Polyphen): Prediction result from PolyPhen-2 (e.g. 'probably damaging', 'possibly damaging', etc.)
  Note: Differentiated between transcripts by '////' as ordered in 1a from above
10b.) Protein_Impact_Probability(Polyphen): Probability score from PolyPhen-2 (e.g. '0.366')
  Note: separated by '////' as ordered in 10a
11a.) Protein_Impact_Prediction(SIFT): Prediction result from SIFT ('INTOLERANT', 'TOLERANT')[note: separated by '////' as ordered in 1a from above]
  Note: Differentiated between transcripts by '////' as ordered in 1a from above
11b.) Protein_Impact_Score(SIFT): Probability score from SIFT
  Note: separated by '////' as ordered in 11a
12a.) Protein_Domains: Names of protein domains in full protein sequence
  Note: Separated by '$' and differentiated between transcripts by '////' as order in 1a
    from above
12b.) Protein_Domains_Impact(LogRE): Names of protein domain impacted by variant
  Note: separated by '$' and differentiated between transcripts by '////' as order in 12a
    from above
  Format: Protein Family ID~logR.E-value of wild-type vs. variant sequence (e.g.
    'PF02137.11~0.1227')
13a.) Protein_Impact_Prediction(Condel): Prediction result from Condel ('deleterious', 'neutral')[note: separated by '////' as ordered in 1a from above]
  Note: Differentiated between transcripts by '////' as ordered in 1a from above
13b.) Protein_Impact_Score(Condel): Probability score from Condel
  Note: separated by '////' as ordered in 13a
14a.) TFBS: Transcription factor binding sites affected
  Note: separated by '////'
  Format: transcription factor name|alternate id|strand (e.g.
    'MA0150.1|NFE2L2|PLUS')
14b.) TFBS_deltaS: Change in motif score as calculated by the position-weighted matrix (e.g. '-1.844')
  Note: separated by '////' as ordered in 14a -continued 15a.) omimGene_ID~omimGene_association: OMIM gene id
    Note: Differentiated between transcripts by '////' as ordered in 1a from above
    Format: OMIM ID~OMIM association (e.g. '601107~Dubin-Johnson syndrome')
15b.) Protein_Domain_Gene_Ontology: Results from InterProScan
    Note: separated by '~' and differentiated between transcripts by '////' as ordered in 1a
        from above
15c.) dbSNP_ID: dbSNP ID, if applicable
15d.) HGMD_Variant~PubMedID: HGMD diseased variant
    Note: separated by '////' for multiple diseases
15e.) HGMD_Gene~disease_association: gene symbol~HGMD disease association
    Note: Differentiated between transcripts by '////' as ordered in 1a from above
15f.) Genetic_Association_Database~PubMedID: Known phenotype associations
15g.) PharmGx~Drug: Known pharmacogenomic associations
15h.) Inheritance~Penetrance: Inheritance and penetrance information from GET-Evidence
Database
    Format: Inheritance ~ Penetrance
15i.) Severity~Treatability: Severity and treatability information from GET-Evidence
Database
    Format: Severity ~ Treatability
16a.) COSMIC_Variant~NumSamples: Cancer variant annotated from the Catalogue Of
Somatic Mutations In Cancer (COSMIC) Database
    Format: Primary Histology ~ Number of cancer samples with variant in the COSMIC
        database
16b.) COSMIC_Gene~NumSamples: Cancer gene annotated from the Catalogue Of Somatic
Mutations In Cancer (COSMIC) Database
    Format: Primary Histology ~ Number of cancer samples with variant in the COSMIC
        database
16c.) MSKCC_CancerGenes: Cancer gene annotated from the Memorial Sloan-Kettering
Cancer Center "CancerGene" Database
    Entries: "Oncogene" and/or "Tumor Suppressor"
16d.) Atlas_Oncology: Cancer gene annotated from the Atlas of Genetics and Cytogenetics
in Oncology and Haematology Database
    Entry: "Atlas_CancerGene"
16e.) Sanger_CancerGenes: Cancer gene annotated from the Sanger Institute's "Cancer Gene
Census" Database
    Format: Primary Histology
16f.) Sanger_Germline_CancerGenes: Germline cancer gene annotated from the Sanger
Institute's "Cancer Gene Census" Database
    Format: Primary Histology
16g.) Sanger_network-informed_CancerGenes~Pval: PIN-Rank cancer genes derived from
the Sanger Institute's "Cancer Gene Census" Database
    Format: Cancer Gene ~ P-value
17a.) SegDup_Region: Known region of segmental duplications
18a.) Gene Symbol: Affected HGNC gene symbols
    Note: separated by '////'
18b.) DrugBank: DrugBank ID
    Note: separated by '$' and differentiated between genes by '////' as ordered in 18a
18c.) Reactome_Pathway: Reactome pathways (e.g. 'GPCR downstream signaling')
    Note: separated by '$' and differentiated between genes by '////' as ordered in 18a
18d.) Gene_Ontology: Gene Ontology ID~association (e.g. 'GO:0030574~collagen catabolic
process')
    Note: separated by '$' and differentiated between genes by '////' as ordered in 18a
18e.) Disease_Ontology: Disease Ontology ID~association (e.g.
'DOID:0050298~Adenoviridae infectious disease')
    Note: separated by '$' and differentiated between genes by '////' as ordered in 18a
19a.) ACMG_Score_Clinical~Disease_Entry~Explanation: American College of Medical
Genetics score category for variant derived from causal associations
    Note: multiple disease entries and explanations separated by '////'
    Format: ACMG Score Category ~ Disease Entry for Variant ~ Functional Explanation
19b.) ACMG_Score_Research~Disease_Entry~Explanation: American College of Medical
Genetics score category for variant derived from all associations
    Note: multiple disease entries and explanations separated by '////'
    Format: ACMG Score Category ~ Disease Entry for Variant ~ Functional Explanation
19c.) Functional_Impact: Functional variant scores across impacted genes
    Note: multiple gene entries and explanations separated by '////'
    Format: Functional Variant Score ~ Impacted Gene ~ Functional Explanation Referring now to the process illustrated in FIG. 3B, the pipeline wrapper 210 may process uploaded variant files. The uploaded variant files are split by chromosomes into separate parts, resulting in 23 separate files. In the illustrative example in FIG. 3B, block 214 represents variants in chromosome 1. Similar blocks represent variants in other chromosomes, respectively.

Annotation generation performed on these 23 files by grouping the annotations set forth above into six separate groups or modules as follows.

The "mapping module" 216 generates the following annotations:

| Gene | Protein_Pos |
|---|---|
| Gene_Type | Original_AA |
| Location | Allele_AA |
| Distance | Start~Stop_Dist |
| Coding_Impact | |

In the mapping module 216, variants may be mapped to nearby gene locations. Gene model and transcript information may be derived from known gene data downloaded from the UCSC Table browser. In some embodiments, the mapping module may also assess coding impact of each variant and report various information such as amino acid changes, distance from the beginning and end of coding sequences, and so forth.

In some embodiments, several types of coding impact may be annotated, including: (1) synonymous (no amino acid change in the protein encoded by the gene); nonsynonymous; nonsense (stop codon mutation); in frame insertion; inter codon in frame insertion (mid-codon insertion of triplet sequences); in frame deletion; in frame deletion of one altered codon (mid-codon deletion of triplet sequences); in frame rearrangement (block substitution of equal bases); frame shift; complex (other block substitutions).

In some embodiments, the pipeline wrapper 210 controls the mapping process so that all the variant files are processed concurrently. In some other embodiments, the variant files may be processed in parallel but not exactly concurrently. In still other embodiments, the variant files may be processed one by one. However, processing multiple variant files at the same time may significantly reduce computing time.

The "non-synonymous-specific module" 218 generates the following annotations:

| | |
|---|---|
| Protein_Impact_Prediction(Polyphen) | Protein_Impact_Prediction(SIFT) |
| Protein_Impact_Probability(Polyphen) | Protein_Impact_Score(SIFT) |

The non-synonymous-specific module may predict whether nonsynonymous mutations may be damaging on resulting proteins based on protein domain conservation, protein structure, chemical, and sequence analysis. The non-synonymous-specific module may predict the impact of amino acid substitution on the structure and function of a protein using classification programs. For example, depending on the classification program used, nonsynonymous mutations may be classified into four categories, such as benign, possibly damaging, probably damaging, and/or unknown. In some embodiments, classifiers that classify mutations may divide the mutations into two categories, such as tolerant and intolerant, damaging and non-damaging, and so/forth.

In some embodiments, analysis using tools such as Polyphen-2 and SIFT may be performed. In some embodiments, the following annotation fields may be generated: prediction result from SIFT (such as intolerant, tolerant, and so forth); protein impact probability score from SIFT; prediction results from PolyPhen-2 (probably damaging, possibly damaging, and so forth); protein impact probability from PolyPhen-2 (a numeric value such as "0.366").

The "transcript-specific module" 218 generates the following annotations:

| | |
|---|---|
| Protein_Domains | Trunc_Prediction |
| Protein_Domains_Impact(LogRE) | miRNA_BS_influenced |
| ESE_sites | miRNA_BS_impact |
| ESS_sites | Splice_Site_Pred |
| Prop_Cons_Affected_Upstream | Splicing_Prediction(MaxENT) |
| Prop_Cons_Affected_Downstream | |

The transcript-specific module may assesses whether mutations may perturb genes based on transcript information. A plurality of analyses may be performed in the transcript-specific module, which may include, for example, determining a log-RE score for protein domains affected by mutations; evaluating if a variant falls near any exon/intron boundaries and whether exonic splicing enhancers and/or silencers may be disrupted; predicting whether a nonsense or frameshift mutation may be disruptive based on whether there may be conserved coding sequence affected by the mutation; determining whether a variant may fall within the 3' UTR region of a gene and predicting whether binding sits may be disrupted either directly or indirectly; and/or predicting whether splicing site donor and acceptor alleles may be perturbed. In some embodiments, the transcript-specific module may search for the presence of conserved sequence motifs that may be involved in RNA splicing, such as 3' splice sites, 5' splice sites, and so forth. Additionally, the transcript-specific module may determine whether protein folding change may result from a mutated protein domain if a variant falls within a functional protein domain.

In some embodiments, tools used by the transcript-specific module may include: HMMER, targetScan, and/or maxENTscan.

In some embodiments, the transcript-specific module may generate the following annotation result fields: protein domains; protein domains impact; Exon Splicing Enhancer ("ESE") sites; Exon Splicing Silencer ("ESS") sites; proportion of affected, conserved, coding sequence upstream of the mutation; proportion of affected, conserved, coding sequence downstream of the mutation; damaging truncation prediction for frameshift/nonsense variants; name of microRNA with an affected binding site; miRNA binding site deletion/creation effect; splice site acceptor/donor disruption; result of MaxENT splice site prediction, and so forth.

The "region-specific module" 218 generates the following annotations:

| | |
|---|---|
| miRNA_genomic | TFBS |
| miRNA_folding_deltaG | TFBS_deltaS |
| miRNA_binding_deltaG | SegDup_Region |
| miRNA_top_targets_changed | Conserved46way |
| miRNA_BS_direct | Conserved46wayPlacental |
| miRNA_BS_deltaG | Conserved46wayPrimates |

The region-specific module may evaluate mutation functionality using region-based information in the variant file. In some embodiments, this module may determine if variants fall within the genomic sequence of miRNA and predict whether the variants may affect maturation and downstream regulation. In some embodiments, the top 5 genes that may be affected may be reported. In some embodiments, this module may also determine if variants fall within the 3'UTR region of a gene and calculate how the variants may affect miRNA binding sites either directly or indirectly. In some embodiments, this module may evaluate the effects of variants on transcription-factor binding sites and predict any likely effect of regulatory functions. In some embodiments, this module may check whether a variant may lie in a region annotated as a segmental duplication region. In some embodiments, the module may also analyze conservation levels based on multiple species alignments based on region level and/or allele-specific level. For example, a variant in a human gene may be compared to conserved variant of the same gene in chimpanzee, monkey, and orangutan genomes, and so forth.

In some embodiments, the region-specific module may predict secondary structures of single stranded RNA by calculating minimum free energy and pair probabilities by taking into account partition function and base pair probability matrix.

In some embodiments, tools executed by the region-specific module during an annotation process may include: RNA fold, RNAcofold, and targetSCAN.

In some embodiments, annotation results generated by the region-specific module may include: name of pre-microRNA sequence that is perturbed; change in minimum free energy of secondary structure of pre-microRNA; average change in Gibbs Free Binding Energy of miRNA to predict 3' UTR binding sites; top 5 genes with largest change in Gibbs Free Binding Energy between microRNA sequence and 3' UTR binding site; name of microRNA with an affected binding site (direct impact), transcription factor binding site affected ("TFBS"), change in motif score as calculated by position-weighted matrix (a numerical score such as "−1.844"); known region of segmental duplications; conservation scores, and so forth.

The "variant-specific module" 218 generates the following annotations:

| | |
|---|---|
| omimGene_ID~omimGene_association | ASW_minallele |
| Protein_Domain_Gene_Ontology | CEU_minallele |
| dbSNP_ID | CHB_minallele |
| HGMD_Variant~PubMedID | CHD_minallele |
| HGMD_Gene~disease_association | GIH_minallele |
| Genetic_Association_Database~PubMedID | JPT_minallele |
| PharmGx_Variants~Drug | LWK_minallele |
| Inheritance~Penetrance | MEX_minallele |
| Severity~Treatability | MKK_minallele |
| COSMIC_Variant~NumSamples | TSI_minallele |
| COSMIC_Gene~NumSamples | YRI_minallele |
| MSKCC_CancerGenes | 1000GENOMES_AF |
| Atlas_Oncology | CG_69_AF |
| Sanger_CancerGenes | CG_WELLDERLY_AF |
| Sanger_Germline_CancerGenes | eQTL_genes |
| Sanger_network-informed_CancerGenes~Pval | |

The variant-specific module may analyze a variant file and determine mutation related functionality. In some embodiments, the variant-specific module may extract known pathogenic information from online databases such as OMIM (Online Mandelian Inheritance in Man) and publications, and use the extracted information to create a database of pathogenic information. In some embodiments, PudMed ID of references may be recorded in the created database. In some embodiments, the variant-specific module may search for protein domain information and/or gene ontology information, and store it in the created database. In some embodiments, the module may annotate and/or assess the variants with known-disease-causing variant information from the Human Gene Mutation Database (HGMD). It may also annotate variants with diseases associations from the Genetic Association Databases (GAD). The module may also annotate and/or assess the variants using known pharmacogenetic associations from databases including BioBase. The variant-specific module may also annotate and/or assess variants using inheritance, penetrance, severity, and treatability of mutation information from GET-Evidence database; variant-specific and gene-specific oncogenic information from COSMIC, and oncogene information from Sanger Institute, Atlas oncology, and Memorial Sloan-Kettering Cancer Center (MSKCC). Network-informed oncogenic associations may also be used with statistical p-values.

According to some embodiments of the disclosure, allele frequency information from databases such as the Complete Genomics 69 genomes diversity panel, 1000 genomes dataset, HapMap dataset, and Wellderly dataset, may also be used to annotate and/or assess the variants. In some instances, frequency of alternate allele at variant position in the HapMap dataset, if known, may also be included. Known eQTL information from National Center for Biotechnology Information (NCBI) may also be used by the variant-specific module.

Depending on the embodiment, the variant-specific module may also create and store allele frequency information from a curated database populated with allele and variant information of individuals who are reported or known to be healthy. In some embodiments, curated genomic data from the healthy individuals are further filtered using criteria such as race, gender, other genetics related information, and so forth in order to create reference allele/variant dataset for downstream analysis, which is discussed further below.

In some embodiments, the variant-specific module may execute tools such as InterproScan. Results of annotation generated by the variant-specific module may include: OMIM Gene-ID; OMIM Gene-Association; protein domain; gene ontology; dbSNP ID; HGMD variant and/or PubMed ID; GAD ID; pharmacogenomic information; inheritance; penetrance; severity; treatability; COSMIC variant and number of samples; COSMIC gene and number of samples; MSKCC cancer genes; Atlas oncology; Sanger cancer genes; Sanger Germline cancer genes; Sanger network informed cancer genes and/or p-values, and so forth.

The "post-annotation module" 222 generates the following annotations

| |
|---|
| Gene_Symbol |
| DrugBank |
| Reactome_Pathway |
| Gene_Ontology |
| Disease_Ontology |
| ACMG_Score_Clinical~Disease_Entry~Explanation |
| ACMG_Score_Research~Disease_Entry~Explanation |
| Functional Impact |

This module may read in variants that have been processed by all other modules and after minor, additional annotations, is ready to be scored by the standards of the American College of Medical Genetics guidelines. It may determine the functional impact of nonsynonymous mutations by leveraging the aggregate scores of other, various prediction algorithms, extract druggable information as reported from the DrugBank database, report all known pathways of genes affected as shown in the Reactome database, report additional Gene Ontology and Disease Ontology information for genes affected, classify variants into appropriate American College of Medical Genetics criteria for clinical use which only includes known, causal associations, and classify variants into appropriate American College of Medical Genetics criteria for research use which includes all associations.

In some embodiments, the post-annotation module may extract druggable information as reported from the DrugBank database. The module may also classify variants into appropriate American College of Medical Genetics ("ACMG") criteria for research and/or clinical use. In some embodiments, the ACMG criteria for clinical use may include known, causal associations. In some embodiments, the ACMG criteria for research use may include all associations.

In some embodiments, the post-annotation module may further create a final annotation file 224. The pipeline wrapper 210 may detect the existence of the final annotation file 224, and import the annotated data into the annotation database 130 as described above.

In the implementation of FIG. 3B, the mapping module 1 is performed in parallel for each of the 23 separate chromosomal files. Then, each of the 23 files is split into four files, and the next four modules designated 218 above are performed in parallel on each of these files. The results from these four modules are collected back into 23 chromosome specific files at 220 of FIG. 3B, and then the final post annotation processing module 222 is performed.

In this implementation, the modules processed in parallel are computationally independent, and are designed to be completed in approximately the same computation time. At 218, for example, the annotations associated with each of the four files are selected so that the time required to perform the database lookups and computations will generally be similar for all the files. This eliminates bottlenecks and data dependencies that can slow the annotation process.

Figure 4:
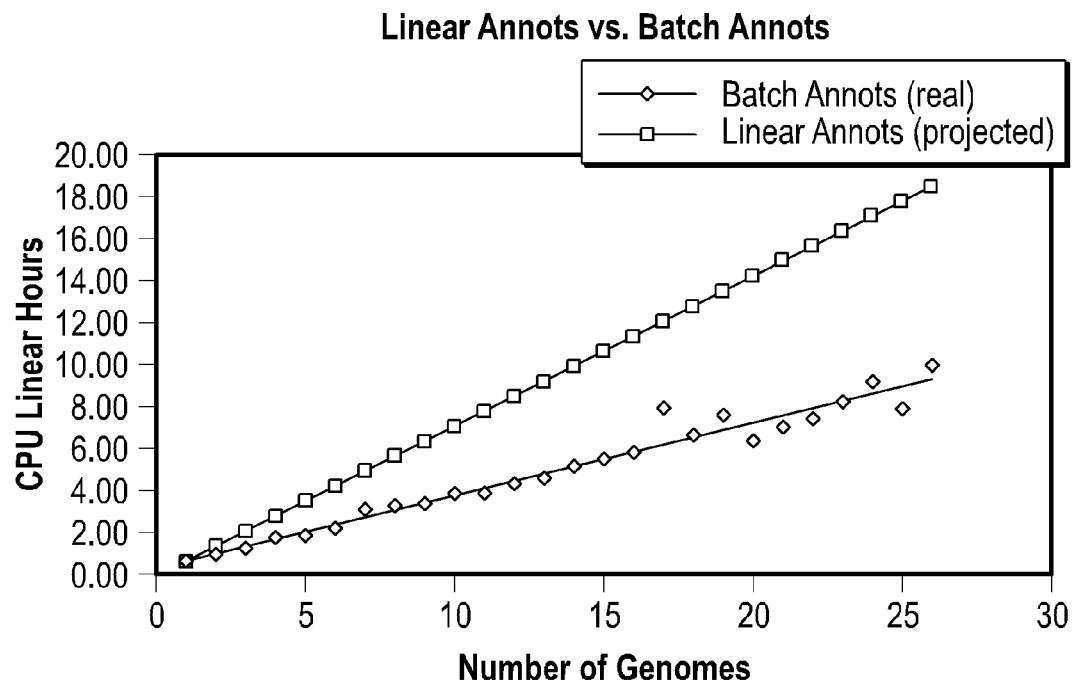
FIG. 4 is a diagram illustrating processing speed improvements of batch variant file annotation.

Further speed improvements can be obtained by annotating variant files in a batch rather than serially. In this implementation, when a wrapper instance is created at block 226 of FIG. 3A, several variant files can be combined into a single variant file, and variants in common between multiple variant files (e.g. by comparing variant location and allele) can be included in the batch file only once, with the annotation controller tracking which file IDs include which variants that will be annotated. After the annotation process, the annotation controller can duplicate the results for each of the original variant files that included the particular common variant. The speed enhancements generated by this batch variant file annotation are illustrated in FIG. 4.

With the variant annotation data placed in the annotation database 130, the application server 120 can build the genotype database 115 of FIG. 1. The genotype database can include the file ID of each annotated variant file, associated with a set of variant IDs that are in the annotation database and have been annotated by the annotation processing computer system 135. The application server can also "curate" the annotation database by finding duplicate annotated variants associated with different file IDs, and retaining only one copy of each annotated variant. In this implementation, the annotation database 130 stores one instance of each different annotated variant generated by the annotation server 135, each having a unique variant ID. The genotype database stores one instance of each file ID for every variant file processed by system 100, and each file ID in the genotype database 115 is associated with the variant IDs of the annotated variants in the annotation database 130 that were in the variant file having that file ID number.

In some implementations, the genotype database 115 may be structured as a graph schema. Open source databases such as HyperGraphDB may be implemented to produce the genotype database 115.

Figure 5:
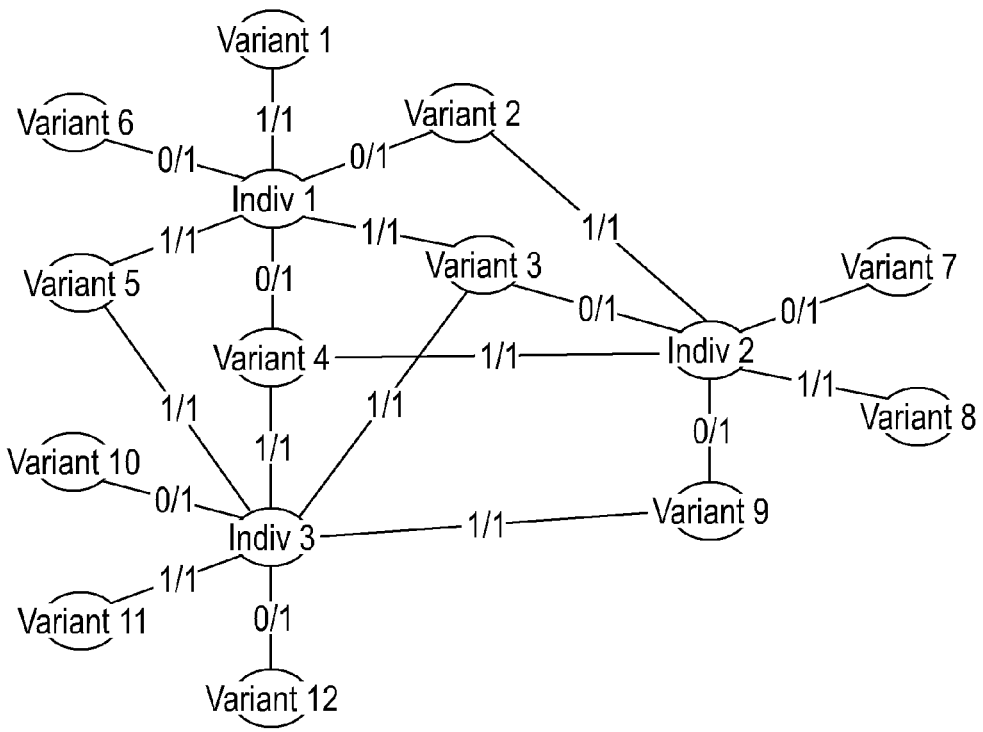
FIG. 5 is a diagram illustrating one embodiment of a graph-oriented data storage system which may include genotype data.

FIG. 5 is a diagram illustrating the structure of a portion of the genotype database 115 implemented as a graph-oriented database. In the illustrative example of FIG. 5, file IDs and variant IDs form nodes of the graph. Edges of the graph connect a file ID node with a variant ID node if the variant associated with the variant ID was in the variant file associated with the file ID. In a graph database structure, nodes and edges can have defined properties. In the example of FIG. 5, a property of each edge defines whether the individual associated with the file ID is homozygous (1/1) or heterozygous (0/1) for the variant associated with the variant ID node. Other properties that edges may have that could be useful include metadata from the original variant file indicating the quality of the sequence process that generated the variant information. In FIG. 5, file ID 1 is associated with six variants. It can be seen as well with this structure that file IDs 1, 2, and 3 all share variant IDs 3 and 4.

Using a graph-oriented genotype data storage system, database queries that are very useful for data mining genomic data can be especially fast and efficient. For example, a query such as how is the individual associated with file ID 1 connected to the individual associated with file ID 2 will output shared variant IDs 2, 3, and 4 faster than such information would generally be available if the same data were stored in a relational database for example. Variant frequency information is also immediately available from this database structure by simply counting the edges associated with a selected variant. It would be possible to also store the annotations in annotation database 130 as properties of the variant nodes of the genotype database 115, at the cost of additional storage space requirements.

To avoid tying up computational resources re-annotating a variant that the system 100 has previously annotated, when a wrapper instance is opened by the annotation processing computer system 135, the variants therein can be compared (e.g. by location and allele) to annotated variants already present in the annotation database 130. For each match that is found, the annotation processing computer system 135 can use some or all of this previously stored information, instead of re-annotating the variant. For annotations generated from curated public database lookups, using earlier data may not be optimal, as the information in the databases is always changing and being updated with new research information. However, other annotations may not be subject to these kinds of changes, and the earlier computed information may be suitable to use again.

It is one aspect of the above described systems and methods that a complex set of a large number of annotations for a whole human genome can be generated in a short period of time. As shown in FIG. 4, even if the batch processing is not performed, the system can annotate whole genome variant files in less than one hour each, or even less than 45 minutes each. The variant files processed at this rate may have an average variant content of more than two million variants per file, and they may be annotated with more than 80 different annotation types, at least 5 of which involve database lookups, and wherein at least some of the annotations are dependent on the value of other annotations for a given variant. With the above described batch annotation processing techniques, whole genome variant lists can be annotated with 80 different annotations in less than 30 minutes per whole genome variant list.

The speed with which so many variants can be annotated with so many complex annotations has a wide variety of important clinical applications. In some applications, whole genome annotation data would be very useful to have, but it is not currently used because of the time traditionally required to generate results and the lack of comprehensiveness of the annotation data previously produced in such efforts. The system could be used to good effect in the context of infectious disease control, neonatal care, and pharmacogenomics.

In a pharmacogenomics application especially, the use of genetically based screens to select appropriate candidates for a drug therapy can have large consequences to the safe and effective use of the drug. This fact has become very important in the design of clinical trials for investigative drugs, as sub-populations with particular genomic characteristics can have widely divergent responses to a drug. The above described annotation systems and methods can be used for detecting a particular variant pattern known or predicted to be significant in a subjects response to a drug, and can also be used to help determine what variant patterns are correlated with different responses to a drug. The rich set of complex annotations generated by the systems and methods described above provides the ability to identify a genomic basis for why particular drugs exhibit toxicity in certain patients and can help identify biomarkers for classifying patients as suitable or unsuitable for a particular drug or other therapy.

Figure 6A:
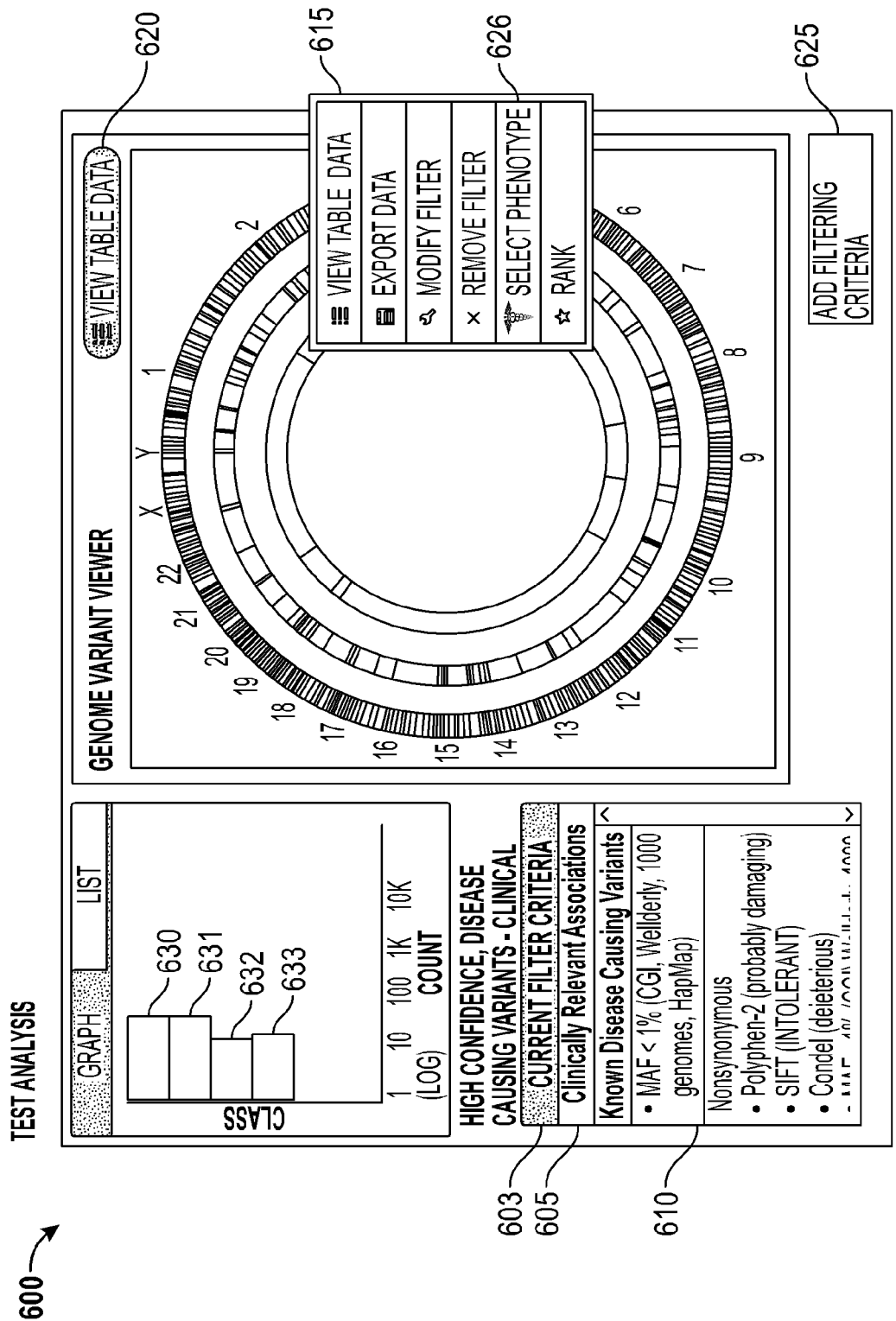
FIGS. 6A and 6B illustrate example user interfaces that may be generated and presented to a user to customize and view genomic variant analysis and annotation results.

FIG. 6A illustrates an example user interface 600 that may be generated and presented to a user to customize and view genomic variant analysis and annotation results. In the example user interface 600, variants may be classified and color-coded or coded with different patterns for viewing convenience. Depending on the embodiments, variants may be grouped and/or classified into groups or types such as truncating mutations 631, damaging nonsynonymous mutations 632, splice site damaging mutations 633, and nonsynonymous mutations 634. More classes and/or types may be displayed for different variants. In some embodiments, a graph may be used to display the number of variants in each class. For example, in the user interface 600, the width of the bars for each class (630, 631, 632, and 633, respectively) may represent the total number of mutations in each class. In some embodiments, the total number of mutations in each class may be represented based on a logarithmic scale.

The user interface 600 also displays a current set of filters. In some embodiments, a default set of filters may be chosen by the system and presented to a user, and the user may customize the set of filters by adding or removing some filters. In some other embodiments, no filter is applied by the system directly, and the user may choose the filters that he or she decides to apply.

In the user interface 600, a current set of filtering criteria comprises, for example, clinically relevant associations 603, known disease causing variants (Allele Frequency (MAF) <5%) 605, nonsynonymous 610, and/or other filtering criteria. Based on these criteria, the 3-ring display may be filtered down from the entire genome, which is represented by the outside circle, to the middle circle.

In some embodiments, if a user right clicks on either one of the three circles in the 3-ring display, the user interface may generate a pop-up menu with further choices. In the user interface 600, right-clicking on the middle circle may result in the display of the menu 615, which presents choices such as view the variant data as a table, export data, modify filter, remove filter, select phenotype, and rank. Moreover, the user interface 600 also presents an option of adding more filtering criteria if the button 625 is clicked.

In some embodiments, the user interface 600 includes a function of searching based on phenotype criteria. For example, a user may choose "select phenotype" 626, and enter words such as "autoimmune disease" to search for variants known to be related to autoimmune diseases. In some embodiments, a user may also enter the name of one or more disease directly and search for variants known to be related to the one or more disease.

Figure 6B:
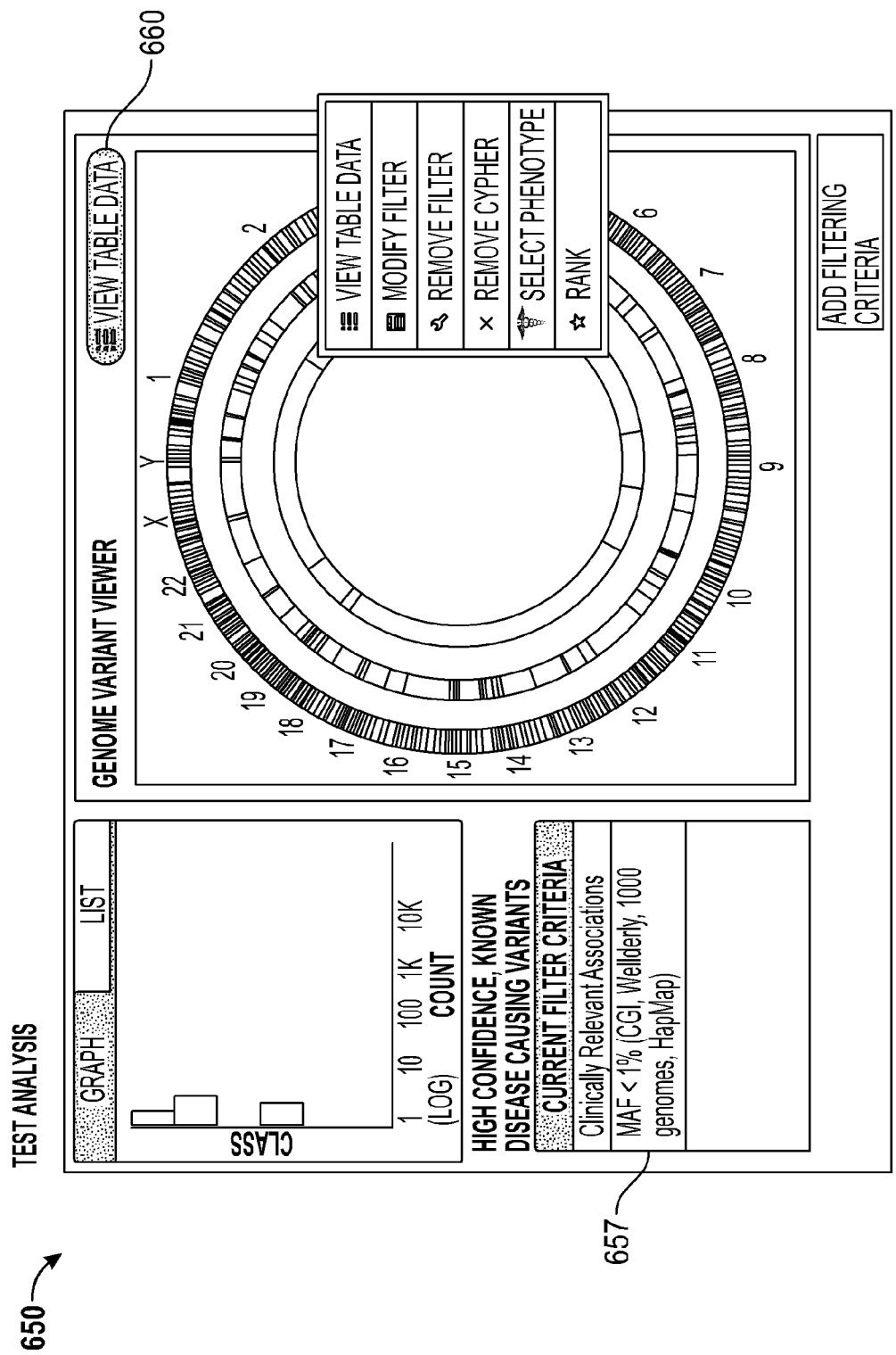

In some embodiments, after adding more filtering criteria, a smaller set of variants may be selected. For example, FIG. 6B shows an example of a user interface 650 wherein additional filtering criteria may be added when a user clicks on the inner-most circle or manually add in more filtering criteria. In this example, when a user clicks on the inner most circle, an additional filtering criteria such as MAF<1% 657, which is more stringent than the criteria 605 in FIG. 6A may be applied to the dataset of variants in the middle circle.

A user may choose to view the results as a table. For example, user interface 600 includes a button 620 which enables displaying of the filtered set of variants as a table. User interface 650 includes a similar button 660 that enables displaying of the filtered set of variants as a table.

FIG. 7 shows an example user interface 700 that may be generated and presented to a user to customize and view genomic variant analysis and annotation results in a table format. In some embodiments, a table may display all the variants filtered using criteria selected by the system or customized by the user. Moreover, in some embodiments, variants may be displayed in a ranked manner according to methods that predict the importance and/or relevance of variants.

In some embodiments, the user interface 700 may also include a button 710 that switches the user interface back to the 3-ring display discussed previously. Depending on the embodiment, the table in user interface 700 may be automatically generated with annotations from the annotation database 130, genotype information from genotype database 115, demographic information from the demographic database 110, and/or other data sources. The information and annotations included in the table in the user interface 700 may include, for example: rank, chromosome name, begin (chromosome position), end (chromosome position), variant type, reference, allele, gene, coding impact, original amino acid, allele amino acid, dbSNP ID, and so forth.

Although the foregoing systems and methods have been described in terms of certain embodiments, other embodiments will be apparent to those of ordinary skill in the art from the disclosure herein. Additionally, other combinations, omissions, substitutions and modifications will be apparent to the skilled artisan in view of the disclosure herein. While some embodiments of the inventions have been described, these embodiments have been presented by way of example only, and are not intended to limit the scope of the inventions. Indeed, the novel methods and systems described herein may be embodied in a variety of other forms without departing from the spirit thereof. Further, the disclosure herein of any particular feature, aspect, method, property, characteristic, quality, attribute, element, or the like in connection with an embodiment can be used in all other embodiments set forth herein.

All of the processes described herein may be embodied in, and fully automated via, software code modules executed by one or more general-purpose computers or processors. The code modules may be stored in any type of computer-readable medium or other computer storage device. Some or all the methods may alternatively be embodied in specialized computer hardware. In addition, the components referred to herein may be implemented in hardware, software, firmware or a combination thereof.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

What is claimed is:

1. A computer-implemented method of increasing the speed of annotating variants from a plurality of subjects, the method comprising:
   receiving a plurality of variant files, the plurality of variant files comprising a plurality of variant lists for a corresponding plurality of subjects, the plurality of variant lists comprising variants found in a plurality of whole or partial genome sequences of the corresponding plurality of subjects, wherein the variants in the lists comprise one or more Single Nucleotide Polymorphisms (SNP), Deletions, Insertions, or Block Substitutions;
   identifying variants in common between multiple variant lists of the received plurality of variant files to identify multiple instances of at least one variant present in the variant lists;
   eliminating all but one instance of the at least one identified variant having multiple instances in the variant lists and combining the plurality of variant files to form a batch variant file comprising a plurality of variants, wherein the identified at least one variant having multiple instances in the received plurality of variant files is included only once the plurality of variants that form the batch variant file;
   generating annotations with an annotation processing system for the plurality of variants that form the batch variant file, and
   storing in an annotation database only one instance of each different annotated variant produced by the annotation processing system.

2. The method of claim 1, additionally comprising duplicating the generated annotations corresponding to the identified at least one variant having multiple instances for each of the received variant files that included the identified at least one variant having multiple instances.

3. The method of claim 1, wherein generating annotations for the variants in the second set comprises generating at least some annotations in parallel.

4. The method of claim 1, further comprising assigning a file identification to each of the received plurality of variant files and tracking which file identifiers are associated with which variants that will be annotated.

5. The method of claim 1, wherein the multiple instances of the at least one variant are identified by comparing variant location and allele.

6. The method of claim 1, further comprising defining a plurality of groups of annotation types, the groups comprising different annotation types from each other.

7. The method of claim 6, further comprising generating annotations for each of the variants in a plurality of parallel processes, the plurality of parallel processes corresponding to the plurality of groups.

8. The method of claim 1, wherein the annotation of the second set of variants comprises identifying a chromosome on which each variant is located.

9. The method of claim 8, further comprising generating annotations for a first set of annotation types for each of the variants in a plurality of parallel processes, the plurality of parallel processes corresponding to the different chromosomes on which the variants are located.

10. A computer-implemented genomic variant annotation system comprising:
    a computer processor;
    an application server that receives a plurality of variant files, the variant files comprising a plurality of variant lists for a corresponding plurality of subjects, the plurality of variant lists comprise variants found in a plurality of whole or partial genome sequences of the corresponding plurality of subjects, wherein the variants comprise one or more Single Nucleotide Polymorphisms (SNP), Deletions, Insertions, or Block Substitutions;
    an annotation controller that receives the variant files from the application server, identifies variants in common between multiple variant files of the received plurality of variant files to identify multiple instances of at least one variant present in the plurality of variant files, eliminates all but one instance of the at least one identified variant having multiple instances in the variant lists, combines the plurality of variant files to form a batch variant file wherein the identified at least one variant having multiple instances in the received plurality of variant files is included only once in the batch variant file;
    an annotation pipeline that receives the batch variant file and generates annotations for the variants that form the batch variant file, and
    an annotation database storing only one instance of each different annotated variant produced by the annotation pipeline.

11. The system of claim 10, wherein the annotation pipeline generates at least some annotations in parallel.

12. The system of claim 10, wherein the application server generates a file identification for each of the plurality of variant files received from the client computer.

13. The system of claim 10, wherein the annotation controller tracks which file identifiers are associated with which variants that will be annotated.

14. The system of claim 13, wherein the annotation controller duplicates the annotation results for each of the multiple instances of the identified at least one variant having multiple instances for each of the received plurality of variant files that included the identified at least one variant having multiple instances.

15. The system of claim 10, wherein the multiple instances of the at least one variant are determined by comparing variant location and allele.

16. The system of claim 10, wherein the annotation pipeline generates annotations for the variants of the batch file by defining a plurality of groups of annotation types, the groups comprising different annotation types from each other.

17. The system of claim 16, wherein the annotation pipeline generates annotations for the variants of the batch file in a plurality of parallel processes, the plurality of parallel processes corresponding to the plurality of groups.

18. The system of claim 10, wherein the annotation pipeline identifies a chromosome on which each variant is located.

19. The system of claim 18, wherein the annotation pipeline generates annotations for the variants in the batch file in a plurality of parallel processes, the plurality of parallel processes corresponding to the different chromosomes on which the variants are located.

20. The system of claim 10, further comprising a client computer that sends the plurality of variant files to the application server and that receives annotation information generated by the annotation pipeline from the application server.

* * * * *